(12) United States Patent
Sugio et al.

(10) Patent No.: US 8,259,169 B2
(45) Date of Patent: Sep. 4, 2012

(54) EYE-GAZE DETECTING DEVICE AND EYE-GAZE DETECTING METHOD

(75) Inventors: Toshiyasu Sugio, Osaka (JP); Daisuke Sato, Osaka (JP)

(73) Assignee: Panasonic Corporation, Osaka (JP)

( * ) Notice: Subject to any disclaimer, the term of this patent is extended or adjusted under 35 U.S.C. 154(b) by 552 days.

(21) Appl. No.: 12/597,264

(22) PCT Filed: Feb. 25, 2009

(86) PCT No.: PCT/JP2009/000826
§ 371 (c)(1),
(2), (4) Date: Oct. 23, 2009

(87) PCT Pub. No.: WO2009/107371
PCT Pub. Date: Sep. 3, 2009

(65) Prior Publication Data
US 2010/0165093 A1  Jul. 1, 2010

(30) Foreign Application Priority Data
Feb. 28, 2008  (JP) ................................ 2008-047044

(51) Int. Cl.
*H04N 7/18* (2006.01)
*G04F 15/16* (2006.01)

(52) U.S. Cl. ........................................................ 348/78

(58) Field of Classification Search ............... 348/78, 348/135
See application file for complete search history.

(56) References Cited

U.S. PATENT DOCUMENTS

| 4,516,157 A | 5/1985 | Campbell |
| 5,579,079 A | 11/1996 | Yamada et al. |
| 5,696,998 A | 12/1997 | Yamada et al. |
| 5,771,402 A | 6/1998 | Yamada et al. |
| 5,912,721 A * | 6/1999 | Yamaguchi et al. .......... 351/210 |
| 5,913,080 A | 6/1999 | Yamada et al. |
| 5,983,029 A | 11/1999 | Yamada et al. |
| 7,046,924 B2 * | 5/2006 | Miller et al. .................... 396/51 |
| 2003/0016332 A1 * | 1/2003 | Trajkovic et al. ............. 351/209 |

(Continued)

FOREIGN PATENT DOCUMENTS

CN  1084728  4/1994

(Continued)

*Primary Examiner* — Zarni Maung
(74) *Attorney, Agent, or Firm* — Wenderoth, Lind & Ponack, LLP (57) ABSTRACT

Accurately and quickly calculated is a calibrating parameter for detecting an eye-gaze coordinate, of an operator, in an input image from a capturing unit worn on a user.

An eye-gaze detecting device (100) detects an eye-gaze coordinate of a user in an input image from a capturing unit (104) wearable on the user, and includes: an eye movement detecting unit (101) detecting an eye movement of the user; a calibration object detecting unit (105) (i) receiving the input image, (ii) determining whether or not there is an object available as a calibration object in the input image, and (iii) providing a position coordinate indicating a position of the object in the case where the available object is determined to be included in the input image; a voice instructing unit (108) providing an instruction to the user to look at the calibration object indicated in the position coordinate; a calibration parameter calculating unit (106) calculating a calibration parameter with a use of the eye movement information of the user receiving the instruction and the position coordinate of the calibration object; and a calibrating unit (102) calibrating the eye movement information to the eye-gaze coordinate with a use of the calculated calibration parameter.

14 Claims, 10 Drawing Sheets

U.S. PATENT DOCUMENTS

| | | |
|---|---|---|
| 2004/0100567 A1* | 5/2004 | Miller et al. .................. 348/239 |
| 2005/0128312 A1* | 6/2005 | Fredlund et al. ........... 348/222.1 |
| 2009/0109400 A1* | 4/2009 | Yoshinaga et al. ............ 351/210 |

FOREIGN PATENT DOCUMENTS

| | | |
|---|---|---|
| JP | 59-107686 | 6/1984 |
| JP | 62-176427 | 8/1987 |
| JP | 1-284227 | 11/1989 |
| JP | 3-62356 | 9/1991 |
| JP | 8-84280 | 3/1996 |
| JP | 2615831 | 6/1997 |
| JP | 11-85384 | 3/1999 |
| JP | 2005-261728 | 9/2005 |
| JP | 2007-25963 | 2/2007 |

* cited by examiner

| Eye potential | Movement angle of eye |
|---|---|
| 5V | 40° |
| 4.5V | 30° |
| 4V | 20° |
| ⋮ | |
| -5V | -40° |

FIG. 4C

| Movement amount of eye | Movement angle of eye |
|---|---|
| 2.0mm | 40° |
| 1.5mm | 30° |
| 1.0mm | 20° |
| ⋮ | |
| -2.0mm | -40° |

FIG. 4B

| Eye potential | Eye-gaze coordinate |
|---|---|
| 5V | 600 |
| 4.5V | 500 |
| 4V | 400 |
| ⋮ | |
| -5V | 20 |

FIG. 4D

| Movement amount of eye | Eye-gaze coordinate |
|---|---|
| 2.0mm | 600 |
| 1.5mm | 500 |
| 1.0mm | 400 |
| ⋮ | |
| -2.0mm | 20 |

| Eye potential | Movement angle of eye | Distance |
|---|---|---|
| 5V | 40° | 1.2m |
| 4.5V | 30° | 1.2m |
| 4V | 20° | 1.2m |
| ... | ... | ... |
| -5V | -40° | 0.5m |

FIG. 10B

| Movement amount of eye | Movement angle of eye | Distance |
|---|---|---|
| 2.0mm | 40° | 1.2m |
| 1.5mm | 30° | 1.2m |
| 1.0mm | 20° | 1.2m |
| ... | ... | ... |
| -2.0mm | -40° | 0.5m | ature
EYE-GAZE DETECTING DEVICE AND EYE-GAZE DETECTING METHOD

TECHNICAL FIELD

The present invention relates to an eye-gaze detecting device and an eye-gaze detecting method for calculating an eye-gaze coordinate, of an image-capturing user, to be provided on an input image via a capturing unit mounted on the head of the user.

BACKGROUND ART

Head-mounted cameras, one of which is disclosed in Patent Reference 1, for example, have been proposed. The head-mounted cameras provide a hands-free capability when capturing an image, so that the user of the camera can capture the image while working on another task. In addition, Patent Reference 2 has proposed to move a capturing position of a capturing unit according to an eye-gaze position of the user. This prevents the capturing position from moving even though the user moves his or her head while capturing the image, and makes possible stable image capturing.

One of the techniques actually moving the capturing position accurately based on the eye-gaze position may be to detect a real-space eye-gaze position of the user with respect to a position on the input image obtained from the capturing unit, and to control the capturing position in order to center the detected eye-gaze position. The following Patent References 3 and 4 exemplify techniques of calibrating the eye-gaze position on the input image to the real-space eye-gaze position of the user.

Described in Patent Reference 3 is a technique to show on a display any given calibration pattern formed in plural dots, to obtain eye movement data in horizontal and vertical directions when the user looks at the dots, and to calculate a calibration parameter according to the data. Patent Reference 3 presents the following techniques for calculating the eye movement data; namely, a corneal-reflection technique, a technique to utilize the difference between a degree of reflection on cornea and that on sclera, a technique to use a contact lens, and the EOG (Electro-Oculography) technique using a generated potential between the cornea and the retina.

In a technique described in Patent Reference 4, plural targets are set as characteristic points on a view image in a surrounding space for preparation of a measurement. Then, a person to be measured wears an eye-camera to sequentially look at the targets. Coordinates as the characteristic points of the watched targets in the view image and coordinate of eye mark signals while the watching are associated each other to be sequentially stored in a table storing unit. When measuring, this correction table with the coordinate stored is used to correct the eye mark signals transmitted from the eye-camera.

Patent Reference 1: Japanese Examined Patent Application Publication No. 3-62356

Patent Reference 2: Japanese Unexamined Patent Application Publication No. 8-84280

Patent Reference 3: Description in Japanese patent No. 2615831

Patent Reference 4: Japanese Unexamined Patent Application Publication No. 62-176427

DISCLOSURE OF INVENTION

Problems that Invention is to Solve

The above conventional techniques face the following problems.

In Patent Reference 3, the calibration pattern is shown on the display. Thus the head-mounted camera with no display cannot provide the calibration pattern to the user, so that the calibration parameter cannot be calculated.

Further, Patent Reference 4 requires: the user in advance to set the targets to be the characteristic points; and the targets to be shown in the capturing unit mounted on the head of the user. This requires the user to have some experience for capturing images as well as it takes extra time to get the image capturing started.

As described, the above conventional techniques need complex preparation for determining the calibration parameter. Thus, the conventional techniques suffer difficulty in readily calculating the calibration parameter in the case where the user is not experienced in the operation, as well as give troubles to the user.

The present invention is conceived in view of the above problems and has an objective to provide an eye-gaze detecting device and an eye-gaze detecting method for accurately and quickly calculating a calibration parameter for detecting an eye-gaze coordinate, of a user, on an input image from a capturing unit wore on the user

Means to Solve the Problems

In order to solve the above problems, an eye-gaze detecting device, which detects an eye-gaze coordinate of a user in an input image from a capturing unit wearable on the user, includes: an eye movement detecting unit which detects an eye movement of the user to obtain eye movement information indicating the eye movement; a calibration object detecting unit which (i) receives the input image, (ii) determines whether or not there is an object available as a calibration object in the input image, and (iii) provides a position coordinate indicating a position of the object in the case where the available object is determined to be included in the input image; an instructing unit which provides an instruction to the user to look at the calibration object indicated in the position coordinate; a calibration parameter calculating unit which calculates a calibration parameter with a use of the eye movement information of the user receiving the instruction from the instructing unit, and the position coordinate of the calibration object, the calibration parameter being used for calibrating the eye movement information to the eye-gaze coordinate; and a calibrating unit which calibrates the eye movement information to the eye-gaze coordinate with a use of the calibration parameter calculated by the calibration parameter calculating unit.

This allows the eye-gaze detecting device in the present invention to quickly and accurately calculate the calibration parameter by the user simply looking at the calibration object indicated in an instruction provided from the instructing unit. Since this requires the user to have no high knowledge, anybody can readily use the eye-gaze detecting device of the present invention.

Further, the calibration object detecting unit may further provide a completion signal when determining that the available object is included in the input image, the completion signal which indicates that the detection of the calibration object has been completed, and the calibration parameter calculating unit may calculate the calibration parameter when receiving the completion signal, the calibration parameter which is calculated with a use of the eye movement information and the position coordinate of the calibration object.

Since the calibration parameter calculating unit renews the calibration parameter after having received the completion signal, this can prevent renewal processing from starting before the user looking at the calibration object. This contributes to more accurate calculation of the calibration parameter.

Moreover, the calibration object detecting unit may (i) extract an amount of image characteristics of the input image, (ii) determine whether or not there is an area having the extracted amount of image characteristics reaching a predetermined threshold, and (iii), when determining that there is the area, provide a position coordinate of the area as the position coordinate of the object available as the calibration object.

Since this makes possible determining the area having a predetermined threshold value in the amount of image characteristics to be an area including the calibration object, the position coordinate of the calibration object and the amount of characteristics can be easily detected.

In addition, the calibration object detecting unit may further provide the extracted amount of image characteristics to the instructing unit when determining that the area has been found, and the instructing unit may provide the instruction to the user to look at the calibration object indicated in the position coordinate and the amount of image characteristics.

This enables the calibration object to be indicated with a use of an amount of characteristics as well as the position coordinate. Hence, the user receiving the indication can easily find the calibration object. Thus, the eye-gaze detecting device in the present invention can (quickly and) accurately calculate the calibration parameter in a short period of time.

Further, the instructing unit may produce navigation information on the calibration object, and provide the produced navigation information to the user as the instruction via voice or bone conduction, the calibration object being indicated in the position coordinate and the amount of image characteristics.

An instruction provided via the voice and the bone conduction enables the user receiving the instruction can easily find the calibration object. Further, utilizing the bone conduction makes possible providing the instruction to look at the calibration object in the case where: the user is: in a noisy environment, or unable to say a word; or a person with visual and hearing disabilities who cannot hear a voice.

Moreover, the calibration object detecting unit may extract at least one of edge information, color information, movement information, and luminance level information as the amount of image characteristics of the input image.

According to the above, extracting the luminance level information, for example, makes possible detecting a visually outstanding area, such as an area having a luminance level higher than the surrounding, as the area including the calibration object. Thus, the user can easily find the calibration object. The same applies in the other kinds of information.

In addition, the calibration object detecting unit may determine whether or not a human face, part of a body of the user, or a belonging which the user is wearing or holding is included in the input image as the object available as the calibration object.

Further, the eye-gaze detecting device may further include a calibration object outputting unit which outputs the calibration object, wherein the instructing unit may provide the instruction to the user in order for the user to look at the calibration object outputted from the calibration object outputting unit.

According to the above, the calibration object output unit outputs a calibration object when no calibration object is detected, for example. Thus, the calibration parameter can be surely renewed with a use of the outputted calibration object.

In addition, the eye-gaze detecting device may further include a distance-to-calibration-object measuring unit which measures distance to the calibration object, wherein the calibration parameter calculating unit may calculate the calibration parameter with a further use of the distance measured by the distance-to-calibration-object measuring unit.

The above procedure allows the eye-gaze coordinate to be accurately calculated out of the eye movement information even in the case where distance between an eye position of the user and the capturing unit is far.

Further, the eye movement detecting unit—may obtain information indicating an eye potential or a movement amount of an eye of the user as the eye movement information.

This allows the eye movement information to be obtained regardless of a shape of an eye of the user, and a capturing environment with a use of, for example, the eye potential. Further, the use of the movement amount of the eye makes possible obtaining more accurate eye movement information.

Moreover, the calibration parameter may be a table associating the eye movement information of the user with the eye-gaze coordinate, the calibration parameter calculating unit may renew the table with a use of the eye movement information of the user and the position coordinate of the calibration object, the user receiving the instruction from the instructing unit, and the calibrating unit may calibrate the eye movement information to the eye-gaze coordinate by referring to the table renewed by the calibration parameter calculating unit.

According to the above, holding the table corresponding the eye movement information with the eye-gaze coordinate makes possible reducing time to be spent for calibration.

It is noted that the present invention can be implemented as an eye-gaze detecting method having characteristic units included in the eye-gaze detecting device as steps, and a program to cause a computer to execute the steps, as well as implemented as the eye-gaze detecting device. As a matter of course, such a program can be distributed via a recording medium such as a CD-ROM and a transmitting media such as the Internet.

Effects of the Invention

As described above, an eye-gaze detecting device in the present invention can quickly and accurately calculate a calibration parameter used for detecting an eye-gaze coordinate, of an image-capturing user, to be provided on an input image via a capturing unit wore on the user.

NUMERICAL REFERENCES 100, 200, 300, and 400 Eye-gaze detecting device
101 Eye movement detecting unit
102 and 402 Calibrating unit
103 Calibration parameter renewal instructing unit
104 Capturing unit
105, 305, and 405 Calibration object detecting unit
106, and 406 Calibration parameter calculating unit
107 Switch
108 Voice instructing unit
209 Calibration object output unit
310 Calibration object registering unit
410 Distance-to-calibration-object measuring unit

BEST MODE FOR CARRYING OUT THE INVENTION

Described hereinafter is an embodiment of the present invention with reference to the drawings.

Figure 1:
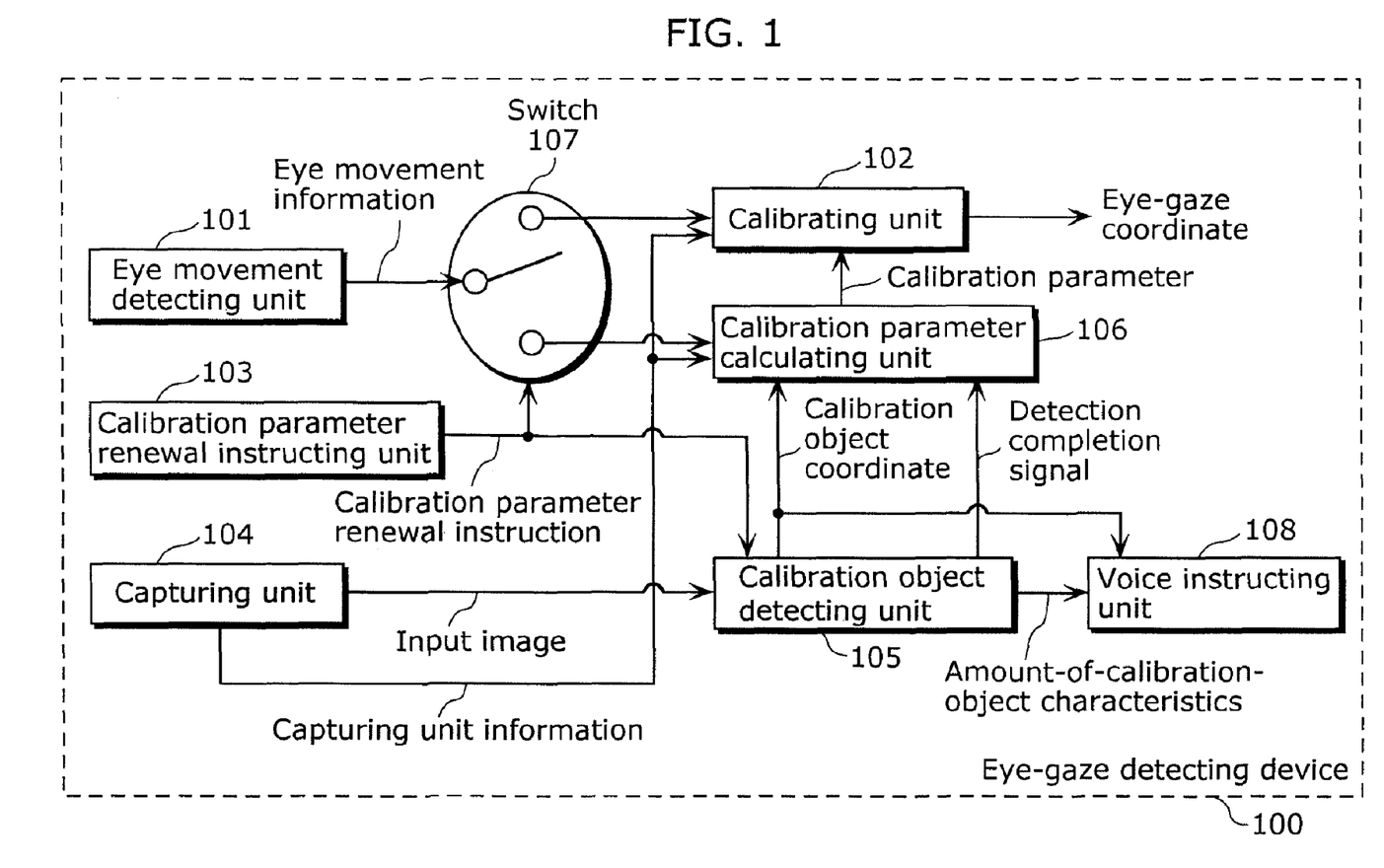
FIG. 1 is a block diagram exemplifying a structure of an eye-gaze detecting device in an embodiment.

FIG. 1 is a block diagram exemplifying a structure of an eye-gaze detecting device 100 in the embodiment. The eye-gaze detecting device 100 in FIG. 1 includes an eye movement detecting unit 101, a calibrating unit 102, a calibration parameter renewal instructing unit 103, a capturing unit 104, a calibration object detecting unit 105, a calibration parameter calculating unit 106, a switch 107, and a voice instructing unit 108.

Figure 2:
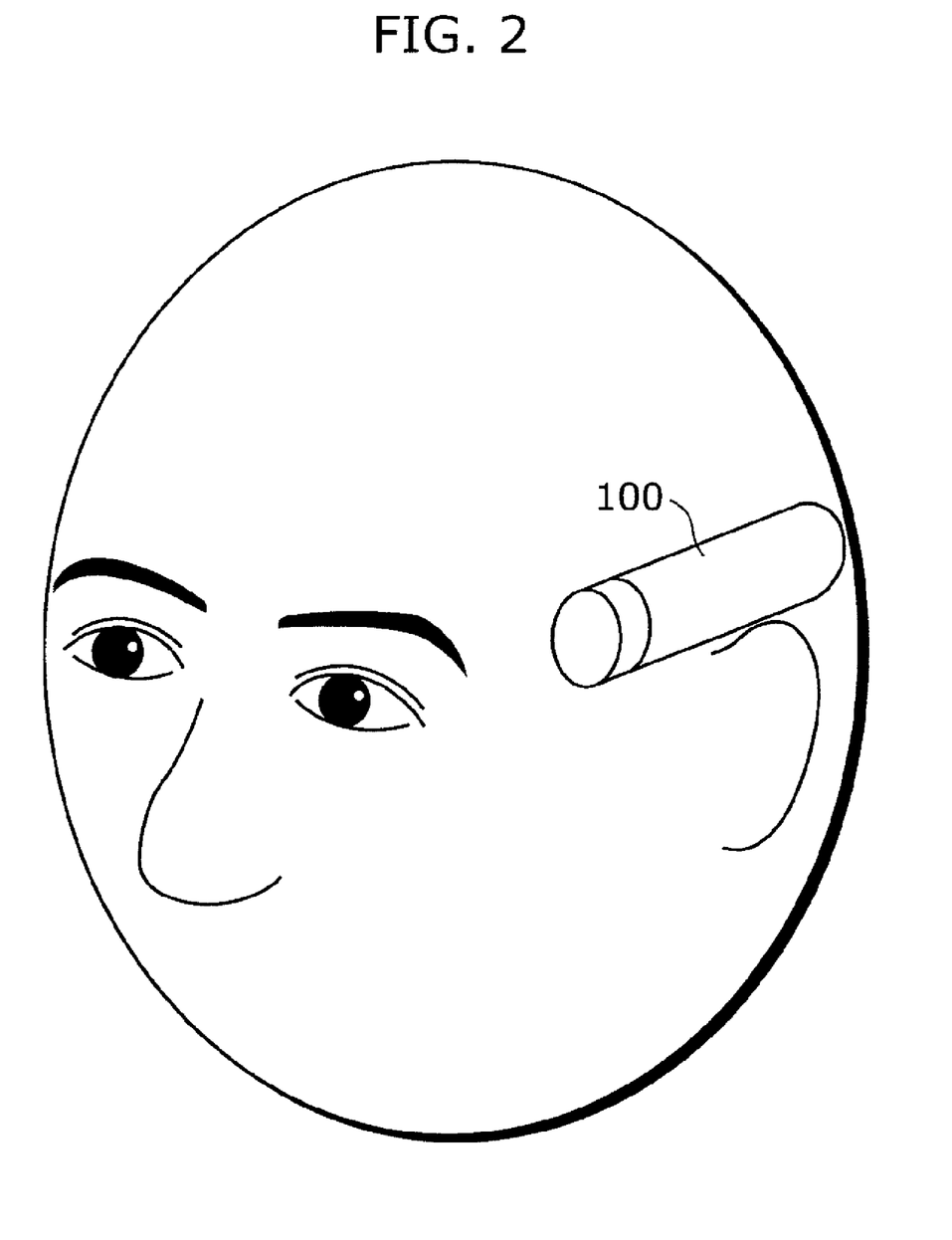
FIG. 2 exemplifies usage of an eye-gaze detecting device in the embodiment.

It is noted, for example, that the eye-gaze detecting device 100 in the embodiment is mounted on the head of the user to capture an image toward an eye-gaze direction of the user, as shown in FIG. 2.

The eye movement detecting unit 101 detects an eye movement of the user so as to obtain eye movement information. For example, the eye movement detecting unit 101 obtains the eye movement information of the user with a use of the following techniques: the EOG technique using a generated potential between the cornea and the retina; a corneal-reflection technique detecting movement of a virtual image created in the cornea, using an incident laser provided into the eye; the scleral reflection method utilizing the difference between a degree of reflection on cornea and that on sclera; and a technique using a contact lens.

The eye movement information: includes the eye potential obtained by the EOG technique, and the movement amount of the eye obtained by the other techniques; and indicates an eye movement of the user. The embodiment exemplifies a case where the eye movement detecting unit 101 utilizes the EOG technique.

The EOG technique is an eye movement detecting technique taking advantage of the fact that cornea of a person is charged positively with respect to retina. Specifically, the EOG technique uses at least one electrode attached in the vicinity of an eye of a person to detect the eye movement according to a varying potential measured by the electrode.

Figure 3:
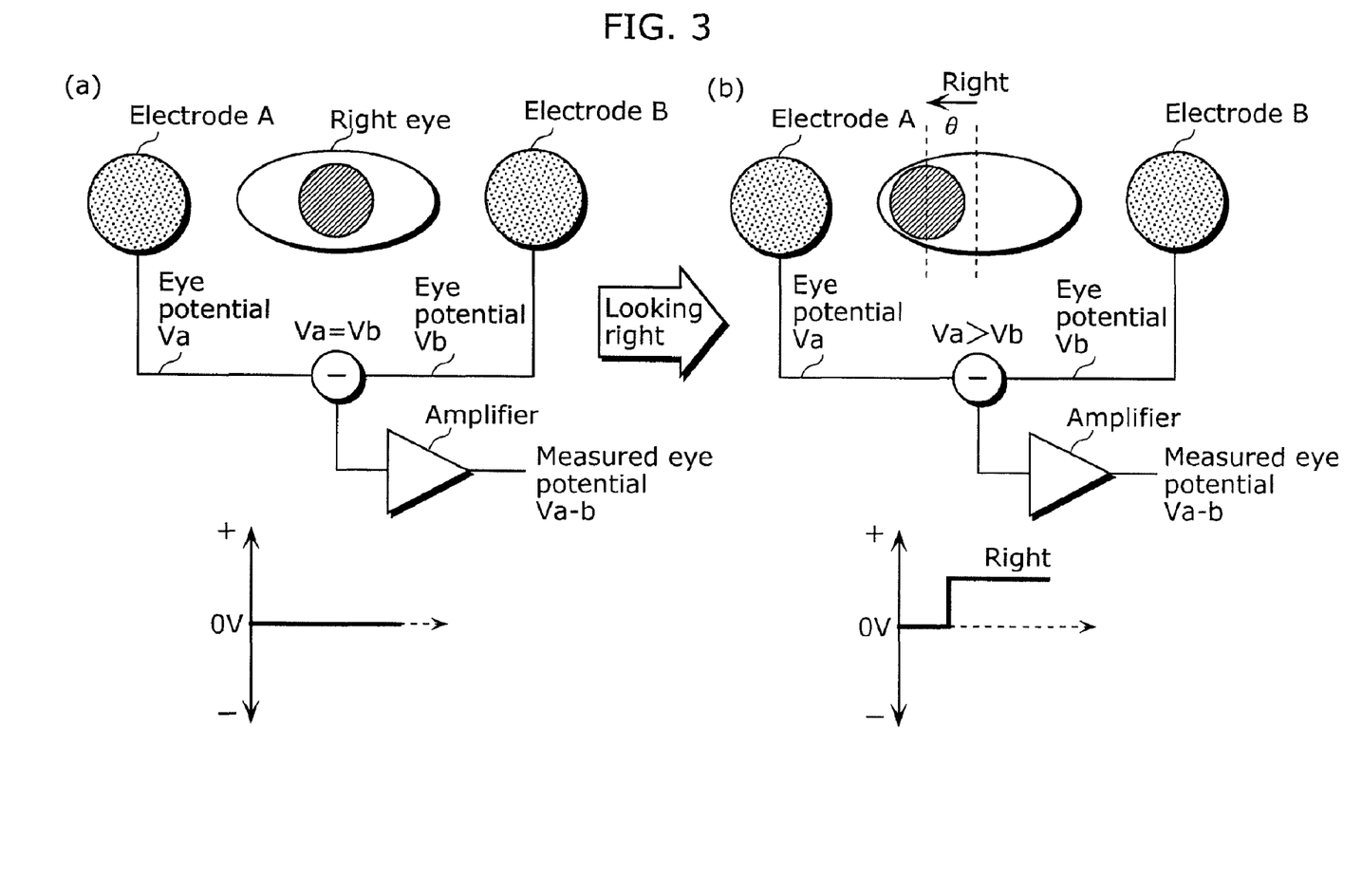
FIG. 3 shows a technique to measure a potential of an eye, using the EOG technique.

FIG. 3 exemplifies an eye movement detecting technique using the EOG technique. In FIG. 3, two electrodes are separated each other at the same distance from the center of the eye, and attached on the left and on the right of the right eye. The electrode attached on the left of the eye is an electrode A, and the electrode on the right is an electrode B.

Assume that an eye potential generated at the electrode A as "Va", and an eye potential generated at the electrode B as "Vb". When the eye of the user is positioned in the middle as shown in FIG. 3(a), "Va" and "Vb" are equal, and the measured eye potential "Va–b" (=Va–Vb) becomes 0V.

When the user looks right, as shown in FIG. 3(b), the electrode A gets closer to the cornea of the right eye. Thus "Va>Vb" is held, and the measured eye potential "Va–b" indicates a positive value. When the user looks left, meanwhile, "Va<Vb" is held, and the measured eye potential "Va–b" indicates a negative value. In other words, a positive value indicated in the measured eye potential "Va–b" finds that the user has moved his or her right eye right, and a negative value finds that the user has moved his or her right eye left.

The EOG technique takes advantage of the above variations of the measured eye potential "Va–b" to detect the eye movement of the user. A typical measured eye potential "Va–b" is known to change in a line shape where a movement angle "θ" of an eye is within a certain scope. In other words, the measured eye potential "Va–b" can be approximated by Expression 1 with a use of a constant "a" and the movement angle "θ" of the eye as follows:

$$Va-b = a \times \theta \quad \text{(Expression 1)}$$

In the embodiment, the constant "a" is referred to as a calibration coefficient.

Referring to FIG. 1 again, the calibrating unit 102 uses a calibration parameter calculated by the calibration parameter calculating unit 106 and capturing unit information provided from the capturing unit 104 to calibrate the eye movement information to an eye-gaze coordinate. In other words, based on the eye movement information obtained by the eye movement detecting unit 101, the calibrating unit 102 uses the calibration parameter and the capturing unit information to calculate the eye-gaze coordinate, of the user, in the input image provided from the capturing unit 104.

Here, the calibration parameter is used for converting the eye movement information into a movement angle of the eye. In other words, the calibration parameter represents a correspondence relationship between the eye movement information and the eye-gaze coordinate. An example of the calibration parameter is the calibration coefficient "a" used in Expression 1. Further, the capturing unit information, obtained from the capturing unit 104, includes lens characteristics, resolution, and an angle of view of the input image.

The following is an operation of the calibrating unit 102 with the EOG method. When an eye potential "Ve" (=Va–b) is provided to the calibrating unit 102 as the eye movement information, an eye movement angle "θe" (=θ) is calculated, using Expression 1. Then, the eye-gaze coordinate is calculated out of the movement angle "θe", using the capturing unit information. Through above procedure, the eye-gaze coordinate can be calculated out of the eye movement information.

Figure 4A:
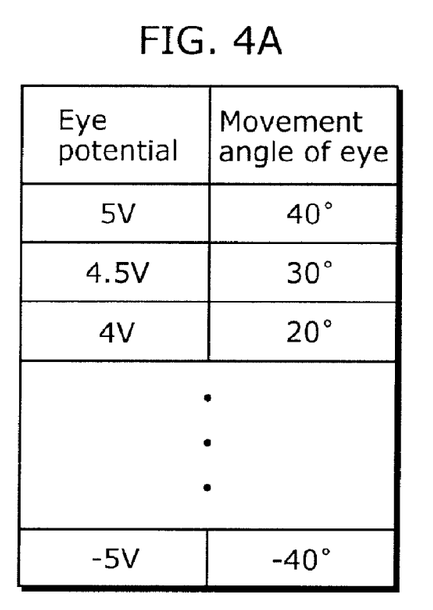
FIG. 4A shows a table associating a potential of an eye with a movement angle of the eye.
Figure 4B:
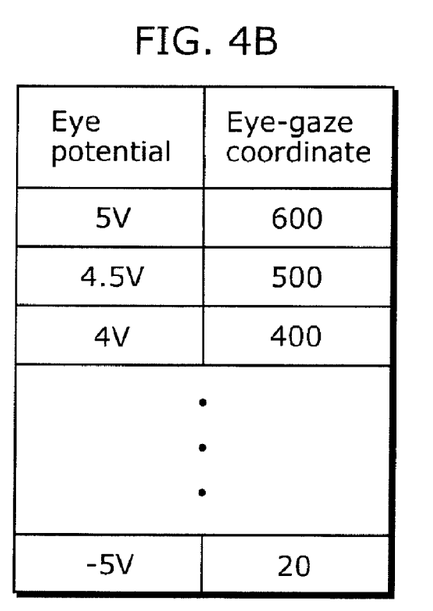
FIG. 4B shows a table associating a potential of an eye with an eye-gaze coordinate.
Figure 4C:
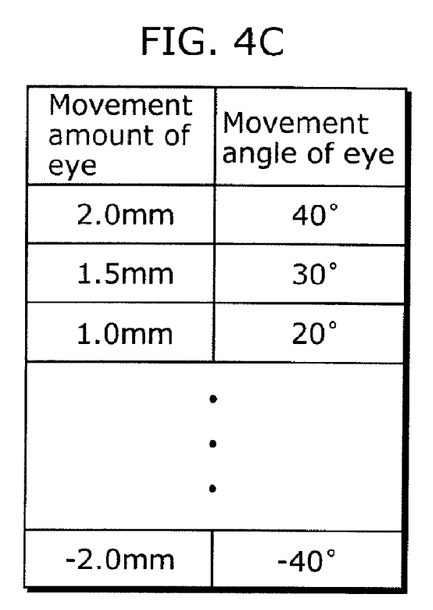
FIG. 4C shows a table associating a movement amount of an eye with a movement angle of the eye.
Figure 4D:
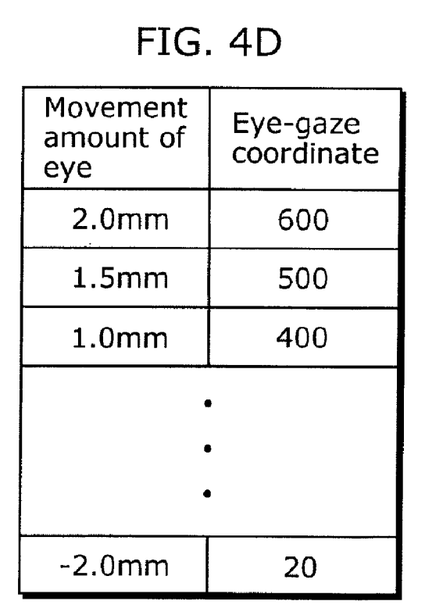
FIG. 4D shows a table associating a movement amount of an eye with an eye-gaze coordinate.

It is noted that the embodiment has described a technique of calibrating with a use of Expression 1; meanwhile, the technique shall not be limited to this. As shown in FIGS. 4A to 4D, for example, the technique may utilize a table associating the eye movement information with the eye-gaze coordinate. FIG. 4A shows a table associating the eye potential with the movement angle of the eye. FIG. 4B shows a table associating the eye potential with the eye-gaze coordinate. FIG. 4C shows a table associating the movement amount of the eye with the movement angle of the eye. FIG. 4D shows a table associating the movement amount of the eye with the eye-gaze coordinate. It is noted for simplicity that both of the movement angle of the eye and the eye-gaze coordinate are shown only in one direction, either in a horizontal or in a vertical direction.

The movement amount of the eye indicates, for example, a movement amount of the center of the pupil when the center of the pupil in the eye facing straight ahead is designated as the reference position. The movement amount of the eye can be obtained by capturing the user's eye with a use of an eye-camera, for example. Further, the eye-gaze coordinate shows a position of the eye-gaze in a horizontal direction or a vertical direction when the upper right corner of the input image is designated as the reference coordinates (0,0). It is noted that any given position may be designated as the reference position and the reference coordinates.

For example, the calibrating unit 102 refers to the table in FIG. 4A to calculate the movement angle of the eye out of the eye potential obtained by the eye movement detecting unit 101. Then, the calibrating unit 102 calculates the eye-gaze coordinate with a use of the capturing unit information according to the movement angle of the eye.

When predetermined events take place, such as the start of capturing the image and a direction from the user, the calibration parameter renewal instructing unit 103 provides a calibration parameter renewal instruction to the calibration object detecting unit 105, the calibration parameter calculating unit 106, and the switch 107.

The capturing unit 104, mounted on the head of the user, captures a view which the user obtains. The captured input image is provided to the calibration object detecting unit 105. Moreover, the capturing unit 104 provides the capturing unit information to the calibrating unit 102 and the calibration parameter calculating unit 106.

When receiving the calibration parameter renewal instruction, the calibration object detecting unit 105 determines whether or not there is any object available as a calibration object included in the input image from the capturing unit 104. Details of the determination shall be described hereinafter with reference to the drawings. Here, the calibration object is a two- or a three-dimensional object which exists in a real space surrounding the user, and has a characteristic form or color, or characteristic brightness. This allows the calibration object to be readily found by the user, and to be easily extracted from the input image through image processing.

When determining that an object available as the calibration object is included, the calibration object detecting unit 105 provides a calibration object coordinate and an amount-of-calibration-object characteristics to the voice instructing unit 108 and the calibration parameter calculating unit 106, respectively. In addition, the calibration object detecting unit 105 provides to the calibration parameter calculating unit 106 a detection completion signal indicating that the detection of the calibration object has been completed.

It is noted that the calibration object coordinate indicates information showing a position of an object, in the input image, determined to be available as the calibration object. The information includes a position coordinate of the object, for example. Further, the amount-of-calibration-object characteristics are information indicating an amount of image characteristics of the object determined to be available as the calibration object. The amount of image characteristics includes an edge, color information, and a luminance level, for example. It is noted hereinafter that the calibration object coordinate and the amount-of-calibration-object characteristics may be collectively-referred to as calibration object information.

When receiving the detection completion signal from the calibration object detecting unit 105, the calibration parameter calculating unit 106 uses, to renew the calibration parameter, the eye movement information, the calibration object coordinate, and the capturing unit information of the user receiving an instruction from the voice instructing unit 108. Specifically, the calibration parameter calculating unit 106 starts to renew the calibration parameter when receiving the detection completion signal from the calibration object detecting unit 105. The following is a calculation example of the calibration coefficient "a"; that is, one of calibration parameters in using the EOG technique.

First calculated is a movement angle "$\theta c$" of the eye of the user looking at the calibration object. "$\theta c$" is calculated out of the calibration object coordinate with a use of the capturing unit information including lens characteristics, resolution, and an angle of view of the input image. Then, an eye potential "Vc" and the movement angle "$\theta c$" of the eye provided as the eye movement information are substituted for Expression 1 to calculate the calibration coefficient "a".

It is noted that when the calibrating unit 102 uses the tables shown in FIGS. 4A to 4D to calculate the eye-gaze coordinate out of the eye movement information, the calibration parameter calculating unit 106 renews values of the tables in FIGS. 4A to 4D. In the case of FIG. 4A, for example, the calibrating unit 102 writes into the table the eye potential and the movement angle of the eye obtained when calibrating, so that the values of the table are renewed.

According to the calibration parameter renewal instruction, the switch 107 switches destinations of the eye movement information obtained by the eye movement detecting unit 101 between the calibrating unit 102 and the calibration parameter calculating unit 106. Specifically, the switch 107 transmits the eye movement information to the calibration parameter calculating unit 106 when the calibration parameter renewal instruction is forwarded. Then, the switch 107 transmits the eye movement information to the calibrating unit 102 when no calibration parameter renewal instruction is forwarded.

When receiving the calibration object coordinate and the amount-of-calibration-object characteristics from the calibration object detecting unit 105, the voice instructing unit 108 uses voice to instruct the user to look at the object detected by the calibration object detecting unit 105; that is, the object indicated in the calibration object coordinate and the amount-of-calibration-object characteristics. For example, when the calibration object detecting unit 105 detects the human face in the right of the input image as the calibration object, the voice instructing unit 108 provides voice navigation to the user, saying "Look at the person's face on the right."

Next described is an operation of the eye-gaze detecting device 100 in the embodiment.

Figure 5:
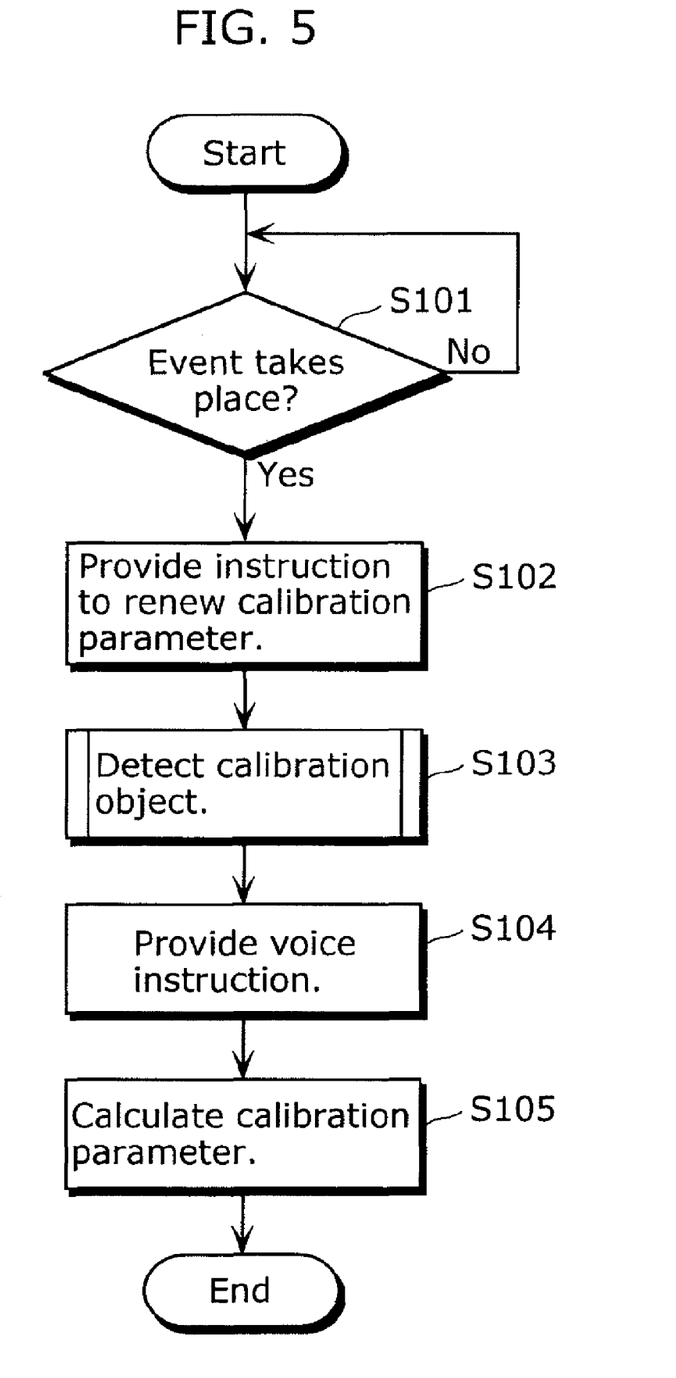
FIG. 5 is a flowchart exemplifying an operation of the eye-gaze detecting device in the embodiment.

FIG. 5 is a flowchart showing the operation of the eye-gaze detecting device 100 in the embodiment.

The calibration parameter renewal instructing unit 103 determines whether or not at least one of the predetermined events has taken place (Step S101). The events include an instruction to start capturing an image, and an instruction, given from the user, to renew the calibration parameter.

In the case where any of the events has not taken place (Step S101: No), the eye-gaze detecting device 100 performs normal detecting of the eye-gaze coordinate instead of performing renewal of the calibration parameter. Here, the calibration parameter renewal instructing unit 103 stands by until the event takes place. In addition, the switch 107 transmits the eye movement information to the calibrating unit 102.

When the event takes place (Step S101: Yes), the calibration parameter renewal instructing unit 103 provides the calibration parameter renewal instruction to the switch 107, and to the calibration object detecting unit 105 (Step S102). The switch 107 receives the calibration parameter renewal instruction to establish a connection between the eye movement detecting unit 101 and the calibration parameter calculating unit 106 in order to transmit the eye movement information to the calibration parameter calculating unit 106.

The calibration object detecting unit 105 receives the calibration parameter renewal instruction to detect the calibration object in the input image forwarded from the capturing unit 104 (Step S103). When detecting the calibration object, the calibration object detecting unit 105 provides the calibration object information to the voice instructing unit 108 and the calibration parameter calculating unit 106. Further, the calibration object detecting unit 105 provides the detection completion signal to the calibration parameter calculating unit 106. Details of the detection of the calibration object shall be described hereinafter with reference to FIG. 6.

The voice instructing unit 108 receives the calibration object information from the calibration object detecting unit 105 and provides a voice instruction to the user, so that the user looks at the calibration object indicated in the received calibration object information (Step S104).

When receiving the detection completion signal from the calibration object detecting unit 105, the calibration parameter calculating unit 106 calculates the calibration parameter (Step S105) with a use of the eye movement information, the calibration object coordinate, and the capturing unit information.

As described above, the eye-gaze detecting device 100 in the embodiment calculates the calibration parameter when calibrating, and calibrates the eye-gaze coordinate according to the eye movement information with a use of the calculated calibration parameter when performing the normal detection.

Figure 6:
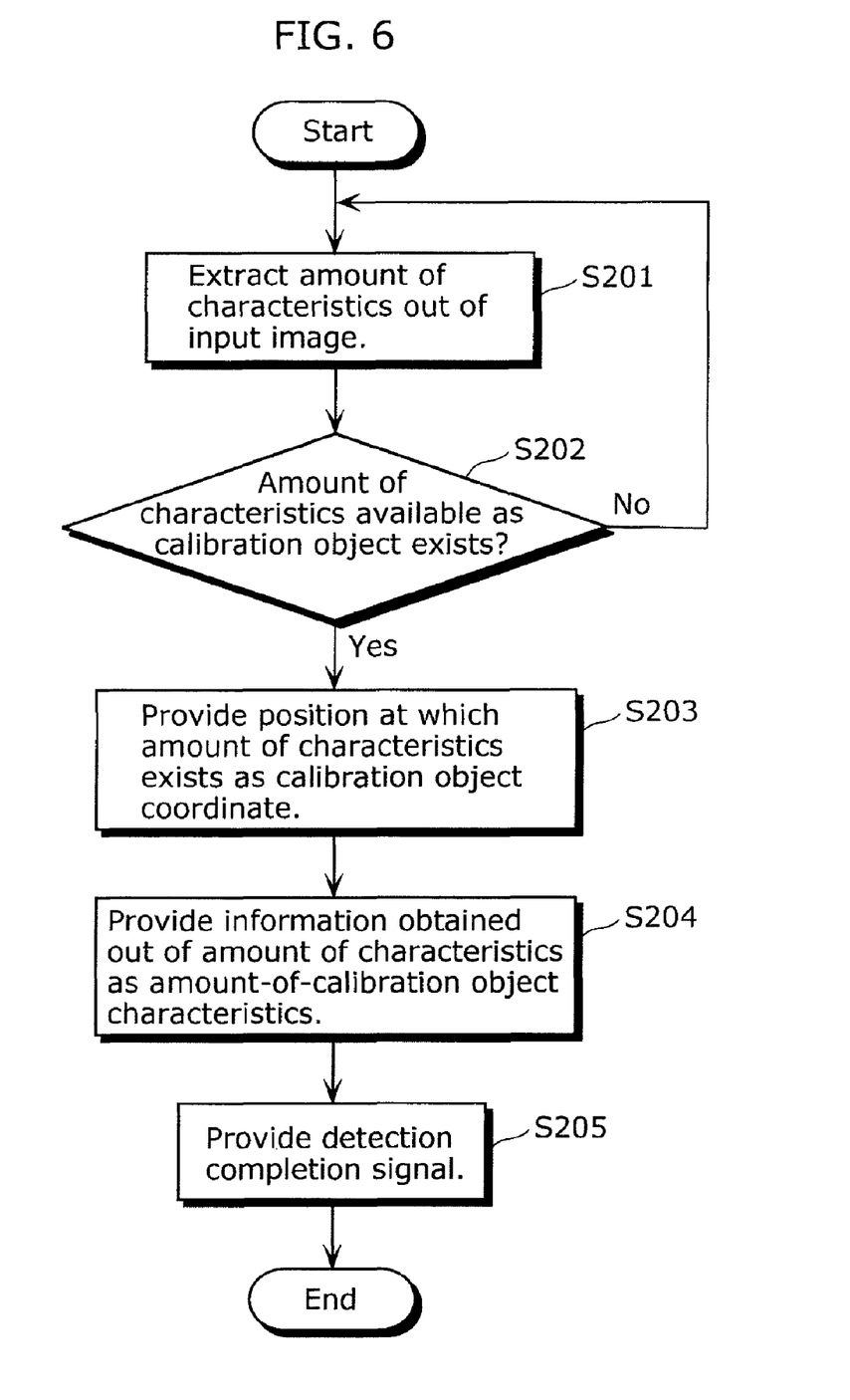
FIG. 6 is a flowchart showing in detail detection of a calibration object according to the embodiment.

Next described with reference to FIG. 6 are details of the detection, of the calibration object, performed by the calibration object detecting unit 105. FIG. 6 is a flowchart showing the details of the detection of the calibration object in the embodiment. It is noted that described hereinafter is an exemplary operation to detect the calibration object by extracting the amount of image characteristics of the input image.

First, the calibration object detecting unit 105 determines whether or not the calibration parameter renewal instruction has been provided, and ends the processing when no calibration parameter renewal instruction is found. When the calibration parameter renewal instruction has been provided, the calibration object detecting unit 105 extracts the amount of image characteristics out of the input image forwarded from the capturing unit 104 (Step S201). Information including an edge, color information, a luminance level, and a movement amount is used for the amount of image characteristics.

Then, the calibration object detecting unit 105 searches for an amount of image characteristics available as the calibration object out of the extracted amount of image characteristics in order to determine whether or not the amount of characteristics available as the calibration object exists in the input image (Step S202). For example, in using the edge information, the calibration object detecting unit 105 determines whether or not there is any predetermined shape, such as a circle and polygonal shapes including a triangle, and a quadrangle, exists. In using the color information, the calibration object detecting unit 105 determines whether or not there is any visually outstanding color including red or blue, such as a color having chroma with a predetermined value or greater. In using the luminance level information, the calibration object detecting unit 105 determines whether or not there is any place brighter than the surrounding; that is, an area having a brightness value higher than the surrounding area. In using the movement amount information, the calibration object detecting unit 105 determines whether or not there is any object having a movement amount with a predetermined value or smaller; that is an object with no movement. Further, a human face and an animal may be used as the amount of image characteristics. As described above, the calibration object detecting unit 105 determines whether or not there is any area, having a predetermined threshold value in the amounts of image characteristics, to be found in the input image.

When no amount of image characteristics is detected in the input image (Step S202: No), the calibration object detecting unit 105 repeats detecting the object available as the calibration object by calculating the amount of image characteristics out of the next input image (Return to Step S201).

When the amount of characteristics available as the calibration object is detected (Step S202: Yes), the calibration object detecting unit 105 designates a position coordinate of the object (area) having the detected amount of characteristics as a calibration object coordinate, and provides the calibration object coordinate to the calibration parameter calculating unit 106 and to the voice instructing unit 108 (Step S203). Further, the calibration object detecting unit 105 designates the information obtained from the detected amount of characteristics as the amount-of-calibration-object characteristics, and provides the amount-of-calibration-object characteristics to the voice instructing unit 108 (Step S204). In addition, the calibration object detecting unit 105 provides to the calibration parameter calculating unit 106 the detection completion signal indicating that the detection of the calibration object has been completed (Step S205).

As described above, the eye-gaze detecting device 100 in the embodiment detects the calibration object in the input image, and shows the user the characteristics and the position in the real-space of the detected calibration object. Then, the eye-gazing detecting device 100 uses the eye movement information, the calibration object coordinate, and the capturing unit information obtained via the user watching the calibration object according to the instruction, and calculates the calibration parameter.

This allows the eye-gaze detecting device 100 to automatically renew the calibration parameter quickly and accurately when renewing the calibration parameter by the user simply moving his or her eye according to the voice navigation provided from the eye-gaze detecting device 100 in the embodiment.

Moreover, the calibration object detecting unit 105 in the eye-gaze detecting device 100 of the embodiment detects an object for the user to be easily found in the real-space out of the real-space. This alleviates troubles which the user faces. Specifically, the calibration object detecting unit 105 detects as the calibration object an object included in an area of which brightness value is higher than the surrounding area, an object in a specific form including a circle and a polygon, and a human face.

In addition, the eye-gaze detecting device 100 in the embodiment detects the calibration object out of the input image. The input image is obtained by the capturing unit 104 capturing an object found in the real-space. In other words, eliminating the need for a display showing the calibration object, the eye-gaze detecting device 100 can readily renew the calibration parameter wherever and whenever.

Described above are the eye-gaze detecting device and the eye-gaze detecting method in the present invention according to the embodiment; meanwhile, the present invention shall not be limited to the embodiment. Those skilled in the art will readily appreciate that many modifications are possible in the exemplary embodiment without materially departing from the novel teachings and advantages of this invention, and therefore, all such modifications are intended to be included within the scope of this invention.

For example, the voice instructing unit 108 produces to provide voice navigation in order to offer an instruction to the user; meanwhile, navigating information other than voice may be produced to offer the user the instruction. Since the eye-gaze detecting device 100 in the embodiment is assumed to be mounted on the head of the user, for example, bone conduction may be utilized to offer the instruction. Meanwhile, visual sense, rather than auditory sense, of the user may be utilized. As an example, a laser pointer may be shined on the detected calibration object to show the user the calibration object to be looked at.

Figure 7:
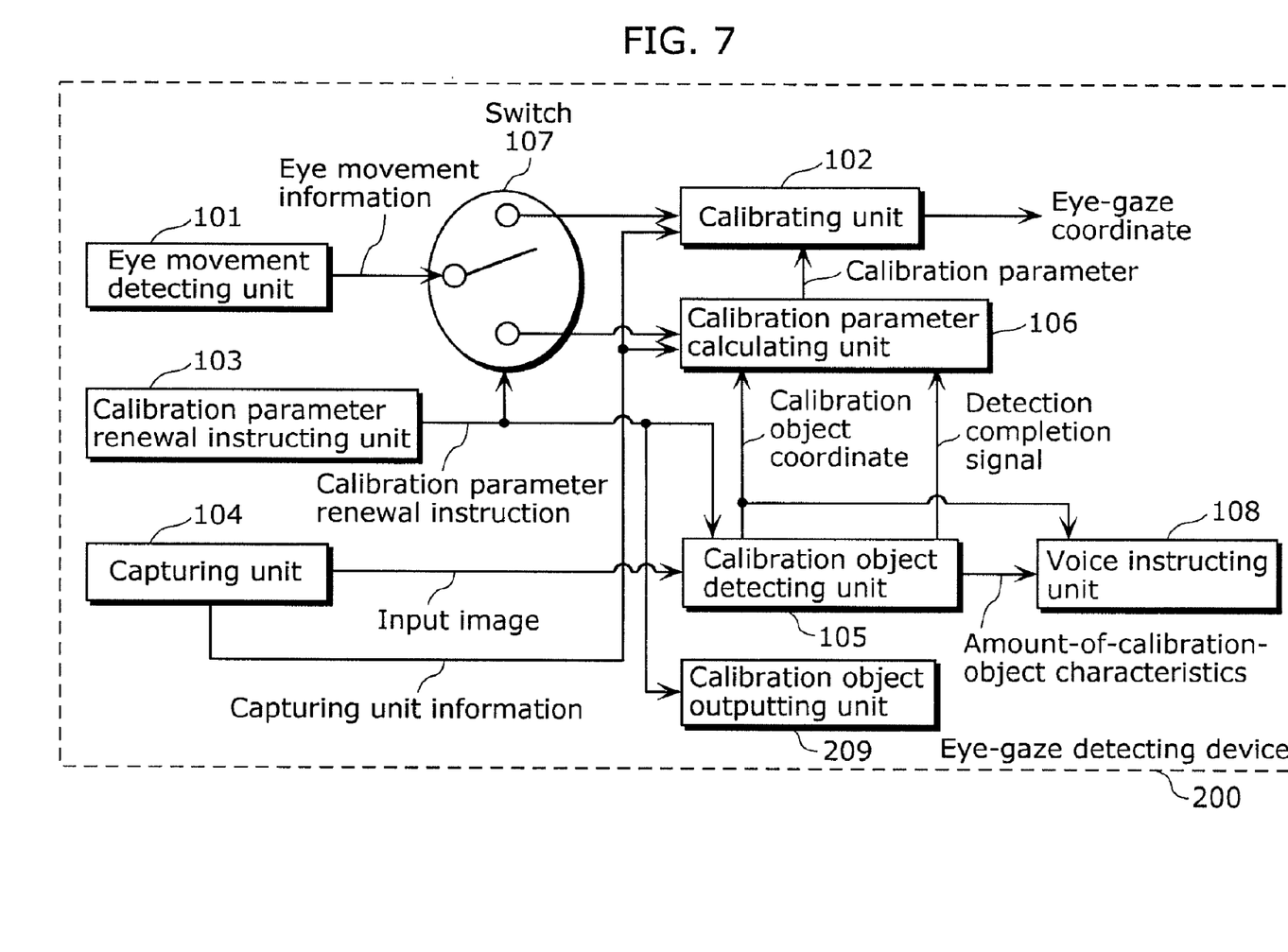
FIG. 7 is a block diagram exemplifying a modification of the structure of the eye-gaze detecting device in the embodiment.

Further, the eye-gaze detecting device in the present invention may be capable of outputting a calibration object to cope with the case where no object for the calibration object is found around the user. FIG. 7 is a block diagram exemplifying a modification of the structure of the eye-gaze detecting device in the embodiment. Compared with the eye-gaze detecting device 100 shown in FIG. 1, an eye-gaze detecting device 200 shown in FIG. 7 is different in additionally including a calibration object output unit 209.

The calibration object output unit 209 outputs the calibration object in the real-space when receiving the calibration parameter renewal instruction from the calibration parameter renewal instructing unit 103. The calibration object is an outputted mark with a use of a laser pointer, and a projector.

This allows the eye-gaze detecting device 100 to automatically renew the calibration parameter quickly and accurately by the user simply looking at the calibration object outputted from the calibration object output unit 209.

It is noted that the calibration object output unit 209 may output the calibration object in the case where the calibration object detecting unit 105 finds in the input image no amount of characteristics available as the calibration object (Step S202: No). This allows the eye-gaze detecting device 200 to renew the calibration parameter even in the case where no object available as the calibration object would be found around the user. Further, when an object available as the calibration object is found, the calibration object output unit 209 outputs no calibration object. Thus, the eye-gaze detecting device 200 can save power use required for outputting the calibration object.

It is noted that when the calibration object output unit 209 outputs the calibration object, the voice instructing unit 108 may show the user a direction of the outputted calibration object. This enables the user to look at the calibration object more easily.

The above is an example of utilizing the amount of image characteristics for the operation of the calibration object detecting unit 105; meanwhile, also utilized may be a technique including template matching comparing a pixel value of an object in the input image with that of a previously registered calibration object.

Figure 8:
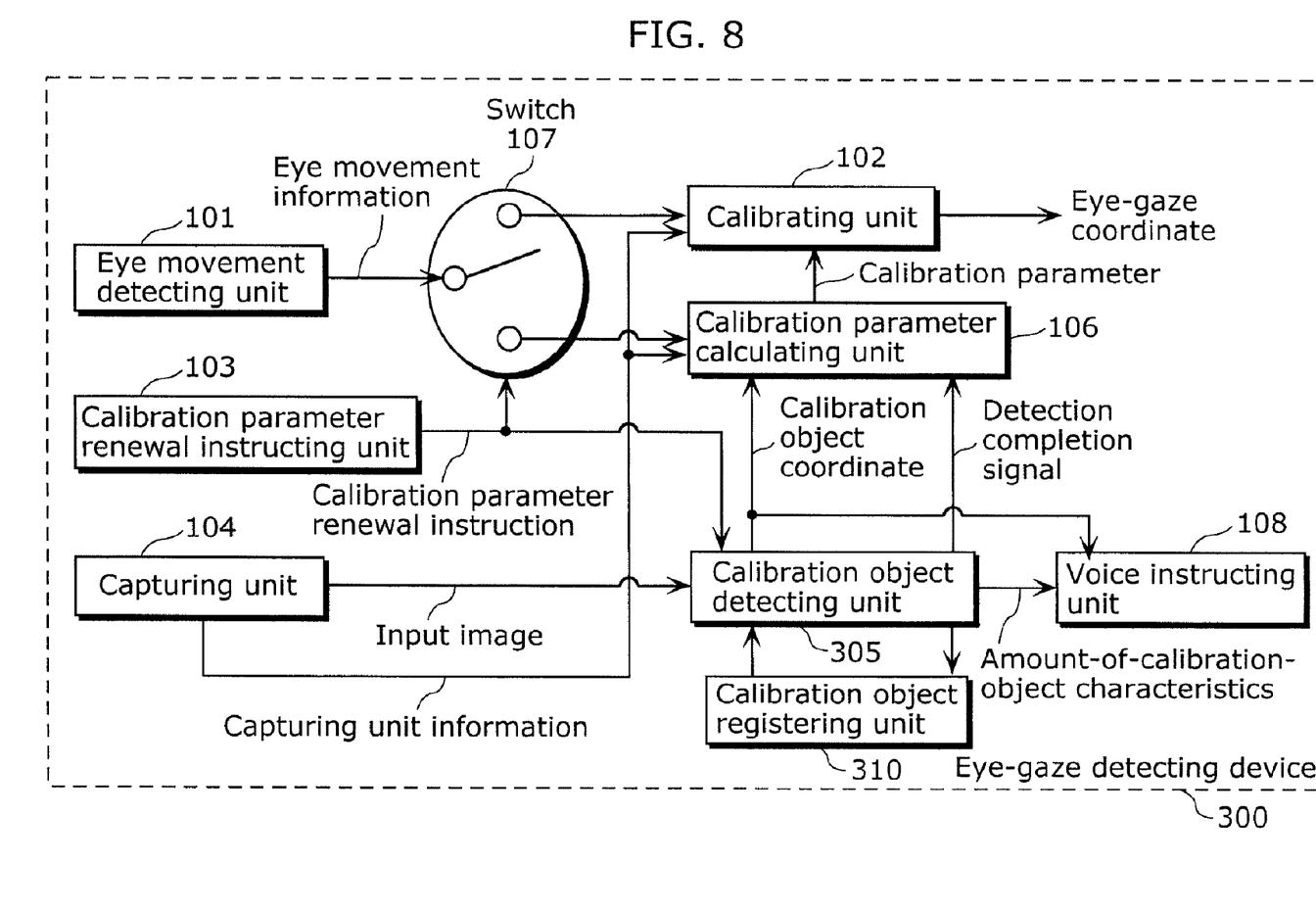
FIG. 8 is a block diagram exemplifying a modification of the structure of the eye-gaze detecting device in the embodiment.

In addition, the calibration object detecting unit 105 may detect, from the input image, an area having an amount of characteristics corresponding to an amount of characteristics previously registered. FIG. 8 is a block diagram exemplifying a modification of the structure of the eye-gaze detecting device 100 in the embodiment. Compared with the eye-gaze detecting device 100 in FIG. 1, an eye-gaze detecting device 300 in FIG. 8 is different in having a calibration object detecting unit 305 instead of the calibration object detecting unit 105, and additionally having a calibration object registering unit 310.

The calibration object registering unit 310 includes a buffer, and stores in the buffer an amount of image characteristics of an object, to be the calibration object, obtained when the capturing unit 104 captures the object. For example, the calibration object registering unit 310 resisters in advance an amount of image characteristics as the calibration object. Here, the amount of image characteristics is obtained when the capturing unit 104 captures a body part, a ring, or a remote control which the user is wearing or holding.

Further, the voice instructing unit 108 may receive the detection completion signal and notify the user of the fact that the calibration object detecting unit 105 has detected the calibration object. The notification may utilize, for example, an alarm sound or vibration instead of a voice.

Figure 9:
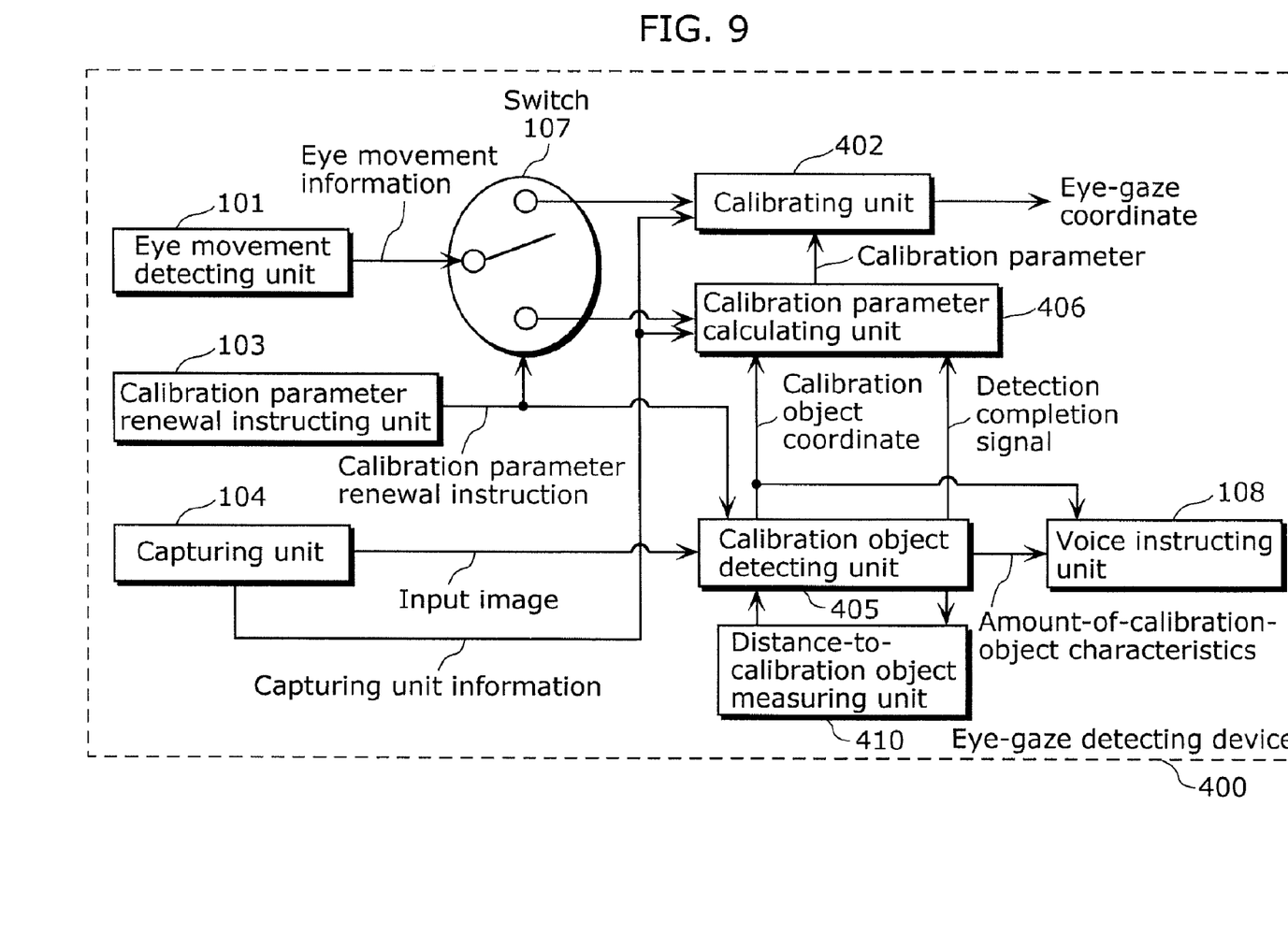
FIG. 9 is a block diagram exemplifying a modification of the structure of the eye-gaze detecting device in the embodiment.

In addition, the calibration object detecting unit 105 may provide as the calibration object coordinate a position coordinate of the calibration object in the input image forwarded from the capturing unit 104, and distance information to the calibration object in the real-space. FIG. 9 is a block diagram exemplifying a modification of the structure of the eye-gaze detecting device 100 in the embodiment. Compared with the eye-gaze detecting device 100 shown in FIG. 1, an eye-gaze detecting device 400 in FIG. 9 is different in: having a calibration object detecting unit 405, a calibration parameter calculating unit 406, and a calibrating unit 402 instead of the calibration object detecting unit 105, the calibration parameter calculating unit 106, and the calibrating unit 102, respectively; and additionally having a distance-to-calibration-object measuring unit 410.

The distance-to-calibration-object measuring unit 410 uses an infrared sensor to measure distance between the eye-gaze detecting device 400 and the calibration object detected by the calibration object detecting unit 405.

The calibration object detecting unit 405 provides to the calibration parameter calculating unit 406 the following as the calibration object coordinate: the position coordinate, of the detected calibration object, in the input image; and distance information "DIS" provided from the distance-to-calibration-object measuring unit 410.

The calibration parameter calculating unit 406 uses the capturing unit information including lens characteristics, resolution, an angle of view of the input image, and the position coordinate of the calibration object to calculate an angle of the calibration object "θcam" with respect to an optical axis of the capturing unit 104. Then, the calibration parameter calculating unit 406 uses the distance information "DIS" of the calibration object to calculate the movement angle "θe" of the eye of the user looking at the calibration object according to the following Expression 2:

$$\tan \theta e = \tan \theta cam + L/DIS \qquad \text{(Expression 2)}$$

where "L" represents distance between an eye position of the user and the capturing unit 104.

Figure 10A:
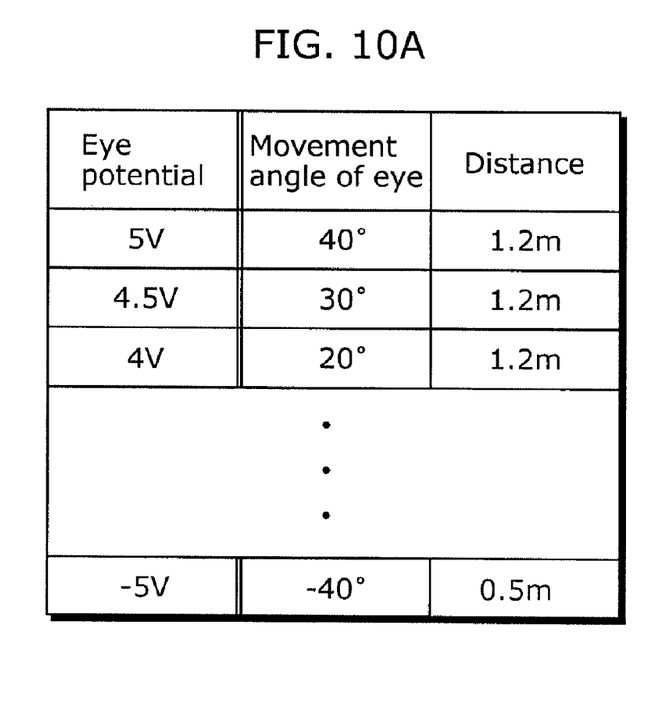
FIG. 10A shows a table associating a potential of an eye with a movement angle of the eye and distance information.
Figure 10B:
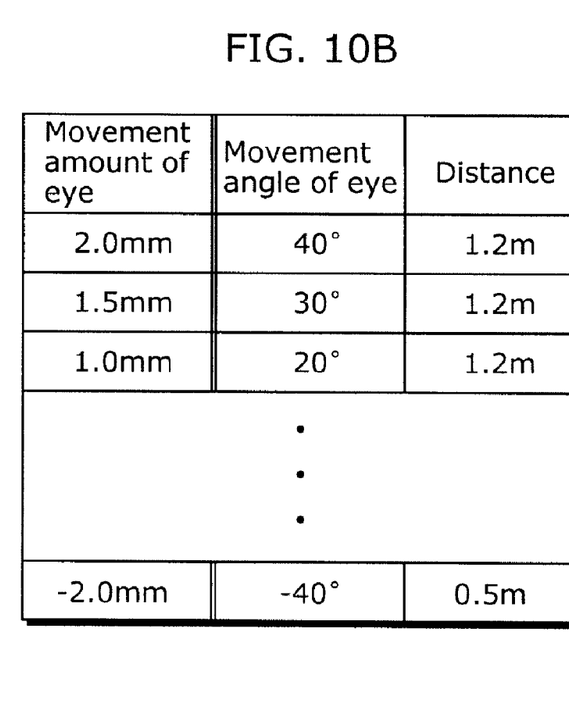
FIG. 10B shows a table associating a movement amount of an eye with a movement angle of the eye and distance information.

Then, the calibration parameter calculating unit 406 renews the values of the tables shown in FIGS. 10A and 10B. In the case of FIG. 10A, for example, the calculating unit 406 writes into the table the eye potential obtained when calibrating, the movement angle of the eye obtained when the user looks at the calibration object, and the distance information to the calibration object, so that the values of the table are renewed.

Further, when receiving the eye potential "Ve" (=Va−b) as the eye movement information, the calibrating unit 402 uses the table in FIG. 10A to obtain the movement angle "θe" of the eye and the distance information "DIS". Then, substituting the movement angle "θe" and the distance information "DIS" for Expression 2, the calibration parameter calculating unit 406 calculates the angle "θcam" of the calibration object, and obtains the eye-gaze coordinate with a use of the capturing unit information. The above procedure allows the eye-gaze coordinate to be accurately calculated out of the eye movement information even in the case where distance "L" between an eye position of the user and the capturing unit 104 is far.

It is noted that the eye-gaze detecting device 100 in the embodiment may omit the capturing unit 104 shown in FIG. 9. Here, the calibration object detecting unit 105 obtains the input image forwarded from an external image capturing device, for example. In addition, the calibrating unit 102 and the calibration parameter calculating unit 106 obtain the capturing unit information forwarded from the external image capturing device.

(The Other Modifications)

The above embodiment has described the present invention; meanwhile, the present invention shall not be limited to the above embodiment, as a matter of course. The following cases shall be included in the present invention.

(1) Specifically, each of the eye-gaze detecting devices described above is a computer system including a micro processor, a Read Only Memory (ROM), a Random Access Memory (RAM), a hard-disk unit, a display unit, a keyboard, and a mouse. The RAM or the hard-disk unit stores a computer program. The microprocessor operates on the computer program, which causes each of the units to implement a function thereof. Here, the computer program includes a combination of plural instruction codes sending an instruction to the computer in order to achieve a predetermined function.

(2) Some or all of the structural elements included in each of the above units may be included in a single system LSI (Large Scale Integration). A system LSI, an ultra-multifunction LSI, is manufactured with plural structural units integrated on a single chip. Specifically, the system LSI is a computer system having a micro processor, a ROM, and a RAM. The RAM stores a computer program. The microprocessor operates on the computer program, which causes each of the units to implement the function thereof.

For example, the structural elements, included in the eye-gaze detecting device 100 shown in FIG. 1, other than the capturing unit 104 and a structural element with a voice producing function removed out of the voice instructing unit 108 may be included in a single system LSI.

(3) Some or all of the structural elements included in each of the above described devices may be included in an IC card or a single module detachable to and from each of the devices. The IC card or the module is a computer system which consists of a micro processor, a ROM, and a RAM. The IC card and the module may also include the above described ultra-multifunction LSI. The micro processor operates on the computer program, which allows the IC card and the module to achieve the function thereof. The IC card and the module may also be tamper-resistant.

(4) The present invention may be in methods described above. The present invention may also be a computer program executing the methods by a computer and a digital signal including the computer program.

The present invention may further include a computer-readable recording medium which stores the computer program or the digital signal into a flexible disk, a hard disk, a CD-ROM, a Magneto-Optical disk (MO), a Digital Versatile Disc (DVD), a DVD-ROM, a DVD-RAM, a Blu-ray Disc (BD) and a semi-conductor memory. The present invention may also be the digital signal recorded in the recording media.

The present invention may further transmit the computer program or the digital signal via a network and data broadcast mainly including an electronic communications line, a wireless or a wired communications line and the Internet.

The present invention may also be a computer system including a micro processor and a memory. The memory may record the computer program described above, and the micro processor may operate on the computer program.

The present invention can be implemented by another independent computer system by storing to transfer the program or the digital signal in a recording medium or via a network.

(5) The present invention may be a combination of the above embodiment with any of the above modification example.

INDUSTRIAL APPLICABILITY

The present invention is effective for a device storing and reproducing an image and a voice in the fields of broadcasting, communications, and accumulation. Further, the present invention can be adapted to a still image storing and reproducing device. Moreover, the present invention can be used as a health and medical device.

The invention claimed is:

1. An eye-gaze detecting device which detects an eye-gaze coordinate of a user in an input image from a capturing unit wearable on the user, said eye-gaze detecting device comprising:
    an eye movement detecting unit configured to detect an eye movement of the user to obtain eye movement information indicating the eye movement;
    a calibration object detecting unit configured to (i) receive the input image, (ii) determine whether or not there is an object available as a calibration object in the input image, and (iii) provide a position coordinate indicating a position of the object in the case where the available object is determined to be included in the input image;
    an instructing unit configured to provide an instruction to the user to look at the calibration object indicated in the position coordinate;
    a calibration parameter calculating unit configured to calculate a calibration parameter with a use of the eye movement information of the user receiving the instruction from said instructing unit, and the position coordinate of the calibration object, the calibration parameter being used for calibrating the eye movement information to the eye-gaze coordinate; and
    a calibrating unit configured to calibrate the eye movement information to the eye-gaze coordinate with a use of the calibration parameter calculated by said calibration parameter calculating unit.

2. The eye-gaze detecting device according to claim 1, wherein said calibration object detecting unit is further configured to provide a completion signal when determining that the available object is included in the input image, the completion signal indicating that the detection of the calibration object has been completed, and said calibration parameter calculating unit is configured to calculate the calibration parameter when receiving the completion signal, the calibration parameter being calculated with a use of the eye movement information and the position coordinate of the calibration object.

3. The eye-gaze detecting device according to claim 2, wherein said calibration object detecting unit is configured to (i) extract an amount of image characteristics of the input image, (ii) determine whether or not there is an area having the extracted amount of image characteristics reaching a predetermined threshold, and (iii), when determining that there is the area, provide a position coordinate of the area as the position coordinate of the object available as the calibration object.

4. The eye-gaze detecting device according to claim 3, wherein said calibration object detecting unit is further configured to provide the extracted amount of image characteristics to said instructing unit when determining that the area has been found, and said instructing unit is configured to provide the instruction to the user to look at the calibration object indicated in the position coordinate and the amount of image characteristics.

5. The eye-gaze detecting device according to claim 4, wherein said instructing unit is configured to produce navigation information on the calibration object, and provide the produced navigation information to the user as the instruction via voice or bone conduction, the calibration object being indicated in the position coordinate and the amount of image characteristics.

6. The eye-gaze detecting device according to claim 3, wherein said calibration object detecting unit is configured to extract at least one of edge information, color information, movement information, and luminance level information as the amount of image characteristics of the input image.

7. The eye-gaze detecting device according to claim 2, wherein said calibration object detecting unit is configured to determine whether or not a human face, part of a body of the user, or a belonging which the user is wearing or holding is included in the input image as the object available as the calibration object.

8. The eye-gaze detecting device according to claim 2, further comprising
a calibration object outputting unit configured to output the calibration object,
wherein said instructing unit is configured to provide the instruction to the user in order for the user to look at the calibration object outputted from said calibration object outputting unit.

9. The eye-gaze detecting device according to claim 2, further comprising
a distance-to-calibration-object measuring unit configured to measure distance to said calibration object,
wherein said calibration parameter calculating unit is configured to calculate the calibration parameter with a further use of the distance measured by said distance-to-calibration-object measuring unit.

10. The eye-gaze detecting device according to claim 2, wherein said eye movement detecting unit is configured to obtain information indicating an eye potential or a movement amount of an eye of the user as the eye movement information.

11. The eye-gaze detecting device according to claim 2, wherein the calibration parameter is a table associating the eye movement information of the user with the eye-gaze coordinate,
said calibration parameter calculating unit is configured to renew the table with a use of the eye movement information of the user and the position coordinate of the calibration object, the user receiving the instruction from said instructing unit, and
said calibrating unit is configured to calibrate the eye movement information to the eye-gaze coordinate by referring to the table renewed by said calibration parameter calculating unit.

12. An eye-gaze detecting method for detecting an eye-gaze coordinate of a user in an input image from a capturing unit wearable on the user, said eye-gaze detecting method comprising:
detecting an eye movement of the user to obtain eye movement information indicating the eye movement;
receiving the input image, determining whether or not there is an object available as a calibration object in the input image, and providing a position coordinate indicating a position of the object;
providing an instruction to the user to look at the calibration object indicated in the position coordinate in the case where the available object is determined to be included in the input image;
calculating a calibration parameter with a use of the eye movement information of the user receiving the instruction, and the position coordinate of the calibration object, the calibration parameter being used for calibrating the eye movement information to the eye-gaze coordinate; and
calibrating the eye movement information to the eye-gaze coordinate with a use of the calibration parameter calculated in said calculating.

13. A non-transitory computer readable medium storing a program causing a computer to execute the eye-gaze detecting method according to claim 12.

14. An integrated circuit which detects an eye-gaze coordinate of a user in an input image from a capturing unit wearable on the user, said integrated circuit comprising:
an eye movement detecting unit configured to detect an eye movement of the user to obtain eye movement information indicating the eye movement;
a calibration object detecting unit configured to (i) receive the input image, (ii) determine whether or not there is an object available as a calibration object in the obtained input image, and (iii) provide a position coordinate indicating a position of the object in the case where the available object is determined to be included in the input image;
an instructing unit configured to provide an instruction to the user to look at the calibration object indicated in the position coordinate;
a calibration parameter calculating unit configured to calculate a calibration parameter with a use of the eye movement information of the user receiving the instruction from said instructing unit, and the position coordinate of the calibration object, the calibration parameter being used for calibrating the eye movement information to the eye-gaze coordinate; and
a calibrating unit configured to calibrate the eye movement information to the eye-gaze coordinate with a use of the calibration parameter calculated by said calibration parameter calculating unit.

* * * * *